United States Patent [19]

Schaus

[11] Patent Number: 4,647,667

[45] Date of Patent: Mar. 3, 1987

[54] OCTA- AND DECA-HYDROQUINOLINE INTERMEDIATES

[75] Inventor: John M. Schaus, Indianapolis, Ind.

[73] Assignee: Eli Lilly and Company, Indianapolis, Ind.

[21] Appl. No.: 776,542

[22] Filed: Sep. 16, 1985

Related U.S. Application Data

[60] Division of Ser. No. 636,959, Aug. 2, 1984, Pat. No. 4,567,266, which is a continuation-in-part of Ser. No. 438,834, Nov. 3, 1982, abandoned.

[51] Int. Cl.$^4$ ............................................. C07D 215/20
[52] U.S. Cl. ................... 546/164; 546/165; 546/178
[58] Field of Search ................ 546/164, 165; 568/346

[56] References Cited

U.S. PATENT DOCUMENTS

| | | | |
|---|---|---|---|
| 3,010,974 | 11/1961 | Barkley | 568/346 |
| 4,198,415 | 4/1980 | Kornfeld et al. | 424/528 |
| 4,230,861 | 10/1980 | Kornfeld et al. | 546/164 |
| 4,235,909 | 11/1980 | Bach et al. | 424/528 |
| 4,501,890 | 2/1985 | Nichols et al. | 514/267 |

FOREIGN PATENT DOCUMENTS 2146992  5/1985  United Kingdom ............... 546/164

OTHER PUBLICATIONS

Streitwieser A. and Heathcock C., *Introduction to Organic Chemistry*, (1976).
Bach et al., *J. Med. Chem.*, 23, 481 (1980).
Johnson et al., *J. Org. Chem.*, 33, 3207 (1968).
Fieser and Fieser, *Reagents for Organic Synthesis*, vol. 7, p. 411.
*Ibid*, vol. 1, p. 382.
Elderfield, *Heterocyclic Compounds*, vol. 5, p. 48.
*C.A.*, 78, 136273j (1973), O.L.S. 2,141,700, 2/22/73.

*Primary Examiner*—Glennon H. Hollrah
*Assistant Examiner*—D. B. Springer
*Attorney, Agent, or Firm*—Charles W. Ashbrook

[57] ABSTRACT

A 1-substituted-3-permissibly-substituted-6 (or 7)-oxodecahydroquinoline is converted to the corresponding 7 (or 6)-formyl derivative. The 6-oxo-7-formyl compound, upon treatment with hydrazine, is cyclized to a tautomeric mixture of 5-substituted-7-permissibly-substituted-4,4a,5,6,7,8,8a,9-octahydro-1H(and 2H)-pyrazolo[3,4-g]quinolines.

8 Claims, No Drawings

OCTA- AND DECA-HYDROQUINOLINE INTERMEDIATES

CROSS-REFERENCE

This application is a division of application Ser. No. 636,959, filed Aug. 2, 1984, now U.S. Pat. No. 4,567,266, issued Jan. 28, 1986, which is a continuation-in-part of my copending application Ser. No. 438,834, filed Nov. 3, 1982, now abandoned.

BACKGROUND OF THE INVENTION

A group of octahydropyrazolo[3,4-g]quinolines is disclosed in Kornfeld and Bach, U.S. Pat. No. 4,198,415 issued Apr. 15, 1980, and in a divisional application thereof, U.S. Pat. No. 4,230,861 issued Oct. 28, 1980. Both intermediates and final products (Ia and Ib below) are disclosed therein.

as compound IX in Reaction Scheme I or as compound XV in Reaction Scheme II where the single tautomer pictured represents both tautomers (as set forth therein). In both reaction schemes, a compound of formula II is converted to the final desired products Ia and Ib by the following generalized reaction scheme.

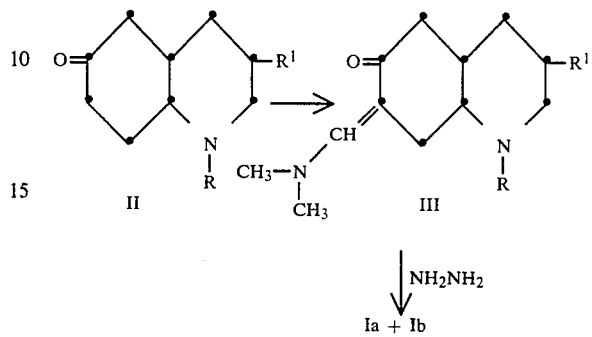

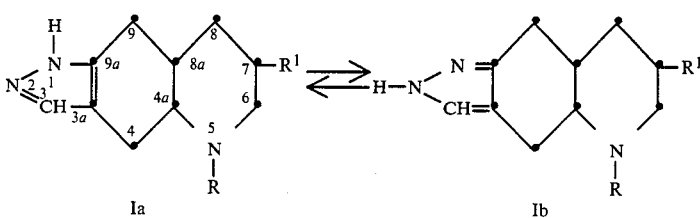

wherein R is H, $C_1$-$C_3$ alkyl, allyl or benzyl, $R^1$ is H or COOY and Y is $C_1$-$C_2$ alkyl or phenyl-substituted $C_1$-$C_2$ alkyl.

Compounds according to these structures (Ia or Ib) are final products where $R^1$ is H and R is $C_1$-$C_3$ alkyl or allyl, or are intermediates where R and $R^1$ are H, where R is benzyl or where $R^1$ is COOY wherein Y is defined as above. Where the compounds according to structures Ia and Ib are final products, they are useful as inhibitors of prolactin secretion and in the treatment of Parkinson's syndrome. Where the compounds are intermediates, they are converted by methods disclosed in the above patents to drugs which are useful in the inhibition of prolactin secretion and in the treatment of Parkinson's syndrome. Compounds according to structures Ia and Ib are to be found in U.S. Pat. No. 4,198,415 as compound IX in Reaction Scheme I or as compound XV in Reaction Scheme II where the single tautomer pictured represents both tautomers (as set forth therein).

The reagent used to transform the 1-substituted 3-permissibly substituted-6-oxodecahydroquinoline (II) to the intermediate (III) is a dimethylformamide acetal such as dimethylformamide dimethylacetal. Compounds of structures II and III are also claimed in U.S. Pat. No. 4,230,861.

DESCRIPTION OF THE INVENTION

This invention provides an improved method of preparing trans-dl-5-substituted-7-permissibly-substituted-4,4a,5,6,7,8,8a,9-octahydro-1H(and 2H)pyrazolo[3,4-g]quinolines. This procedure is set forth in Reaction Scheme I below:

Reaction Scheme I

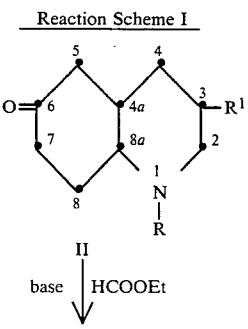

base | HCOOEt

-continued
Reaction Scheme I

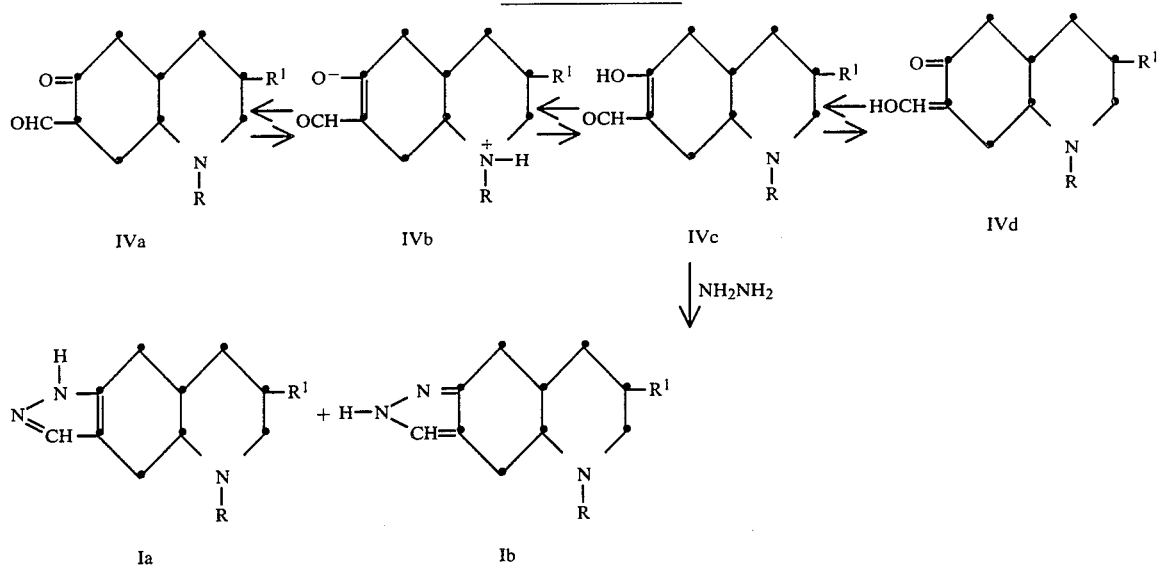

wherein R is $C_1$-$C_3$ alkyl, allyl or benzyl, $R^1$ is H or COOY and Y is $C_1$-$C_2$ alkyl or phenyl-substituted $C_1$-$C_2$ alkyl.

According to Reaction Scheme I, a trans-dl-1-substituted-3-permissibly-substituted-6-oxodecahydroquinoline (II) is formylated with a lower alkyl formate, illustratively ethyl formate, in the presence of base to yield a trans-dl-1-substituted-3-permissibly-substituted-6-oxo-7-formyldecahydroquinoline, represented as a series of tautomeric structures (IVa-d) This intermediate is ordinarily not isolated and characterized as such but is reacted immediately in situ with hydrazine in aqueous THF solution at a pH of about 9 to yield, as a mixture of tautomers, trans-dl-5-substituted-7-permissibly-substituted-4,4a,5,6,7,8,8a,9-octahydro-1H-pyrazolo[3,4-g]quinoline (Ia) and trans-dl-5-substituted-7-permissibly-substituted-4,4a,5,6,7,8,8a,9-octahydro-2H-pyrazolo[3,4-g]quinoline (Ib).

The formylated product, described above as four tautomeric structures (IVa-d), probably exists predominantly in aqueous solution as a zwitterion (IVb). However, all four tautomeric forms are in dynamic equilibrium, and in this specification, if any single structure is pictured or described, the other three are implied and contained therein. The compounds can be isolated in the form of a cationic salt as for example, an alkali metal salt (K,Na), an alkaline earth metal salt (Ca,Mg), a salt of another metal, such as Zn and Al, or a salt formed with a metalloid such as an ammonium ($NH_4^+$), piperazinium, 2-hydroxy ethylammonium etc.

The first step of the above reaction is a modification of a Claissen condensation wherein a methylene group activated by an adjacent carbonyl group can be alkylated in the presence of base. The base commonly employed is sodium ethylate. However, as will be apparent to those skilled in the art, other bases such as the alkali metal t-butoxides and hydrides, specifically, potassium t-butoxide or sodium hydride, can also be used. The Claissen condensation reaction (II→IV) is also usually carried out in ethanolic solution. As will also be apparent to those skilled in the art, other lower alkanols and similar polar anhydrous solvents can be employed as reaction media. I prefer to use tetrahydrofuran as the solvent for the entire reaction scheme pictured in Reaction Scheme I. In the ring closure step, IV→Ia+Ib, hydrazine is specified but hydrazine hydrate or hydrazine salts such as hydrazine hydrochloride can be used with equal success.

Surprisingly, acylation takes place for all practical purposes, exclusively at C-7 despite the fact that the C-5 carbon is also alpha to the carbonyl and also contains two secondary hydrogens.

It is an advantage of the synthetic route described in Reaction Scheme 1 that both steps of the procedure can be carried out in the same reactor; i.e., it can be a "one-pot" process. Secondly, the yields of the pyrazole tautomers (Ia+Ib) are superior to those encountered with the process of the prior art in which dimethylformamide dimethylacetal is reacted with the ketone (II) to form an intermediate 7-dimethylaminomethylene derivative which is in turn reacted with hydrazine to yield the pyrazole tautomers. An additional advantage of this novel process is the fact that, whereas the intermediate enaminoketone and the final product from the prior art synthesis required purification by column chromatography, the final product from Reaction Scheme I is obtained in a sufficiently pure state that chromatography is not required. A further advantage of my novel synthetic route is that the formylating chemical employed, ethyl formate, is relatively inexpensive compared to dimethylformamide dimethylacetal used in the prior art synthesis for a similar purpose.

As set forth in U.S. Pat. No. 4,198,415 in Column 2, each of the tautomers represented by Ia and Ib above exists as a racemic mixture, hence the description trans-dl-. In the case of the 2H-pyrazolo[3,4-g]quinoline, represented as Ib above, these two stereoisomers can be delineated as follows:

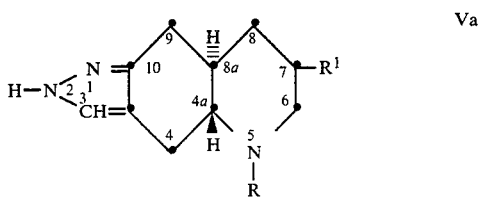

Va

-continued and

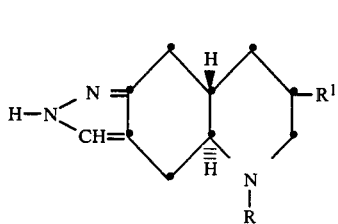    Vb

Va in the instance when R is n-propyl and R' is H can be named 4aR,8aR-5-n-propyl-4,4a,5,6,7,8a,9-octahydro-2H-pyrazolo[3,4-g]quinoline and Vb can be named 4aS,8aS-5-n-propyl-4,4a,5,6,7,8,8a,9-octahydro-2H-pyrazolo[3,4-g]quinoline.

The two stereoisomers represented by formula Ia—the 1H-pyrazolo[3,4-g]quinolines—have the following structures.

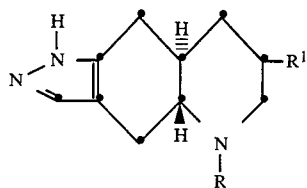   Vc and

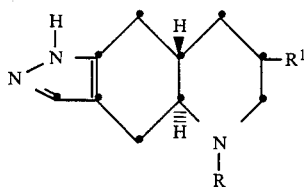   Vd

In the instance where R is n-propyl and R¹ is H, these stereoisomers can be named as 4aR,8aR-5-n-propyl-4,4a,5,6,7,8,8a,9-octahydro-1H-pyrazolo[3,4-g]quinoline (Vc) and 4aS,8aS-5-n-propyl-4,4a,5,6,7,8,8a,9-octahydro-2H-pyrazolo[3,4-g]quinoline (Vd).

The resolution of these tautomeric racemates into their respective stereoisomeric tautomers (Va⇌Vc or Vb⇌Vd) is set forth in the co-pending application of Titus et al. Ser. No. 439,238, filed 11-3-82.

When R¹ is other than H, compounds represented by II above have optical centers at C-3, 4a and 8a. When R¹ is hydrogen, however, the number of optical centers is decreased to two, at C-4a and C-8a, thus yielding two racemic pairs. It should be pointed out the the numbering of the ketone starting material, II, is different from that of the pyrazole final product, I. Thus, the asymmetric bridgehead carbon adjacent to the quinoline nitrogen is numbered 8a in the ketone while it is numbered 4a in the pyrazole. Furthermore, the other asymmetric bridgehead carbon is numbered 4a in the ketone while it is numbered 8a in the final product. These racemic pairs are ordinarily referred to as a cis-dl pair and a trans-dl pair. The configuration of the molecule at C-4a and C-8a in the cis-dl pair would be 4aR, 8aS, and 4aS, 8aR and for the trans-dl pair, 4aR, 8aR, and 4aS, 8aS. These starting chemical configurations are of course maintained in the synthesis of the pyrazoloquinoline since the Claissen consensation and subsequent ring closure with hydrazine do not affect configuration at these optical centers.

The procedure for preparing the decahydroquinolines according to formula II is stereoselective and yields primarily the trans-dl racemate—see U.S. Pat. Nos. 4,198,415 and 4,230,861.

My copending application Ser. No. 384,817 filed June 3, 1982, now abandoned, continuation-in-part of Ser. No. 521,863, filed Aug. 10, 1983, now U.S. Pat. No. 4,540,787, issued Sept. 10, 1985, discloses an improved method of preparing trans-dl-1-n-propyl-6-oxodecahydroquinoline.

The copending application of Schaus and Booher, Ser. No. 439,107 filed 11-3-82, now U.S. Pat. No. 4,471,721, issued Aug. 11, 1984, describes a method of separating trans-dl-1-n-propyl-6-oxodecahydroquinoline (II where R is n-propyl and R¹ is H) into its component stereoisomers IIa (4aR,8aR) and IIB (4aS,8aS).

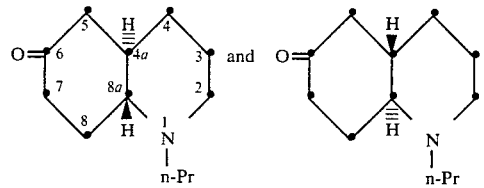

IIa            IIb

The procedure of this invention is as applicable to the separated isomers as it was to the trans-dl-racemate, as in Reaction Scheme I. Titus et al. (loc. cit.) have determined that substantially all of the prolactin inhibiting activity and activity in alleviating the symptoms of Parkinsonism, resides in the 4aR,8aR- or trans-(—)-isomer (Va and Vc wherein R¹ is H and R is methyl, ethyl, n-propyl or allyl) of trans-dl-5-substituted-4,4a,5,6,7,8,8a,9-octahydro-1H(and 2H)-pyrazolo[3,4-g]quinoline (Ia and Ib). This derivative is prepared from the 4aR,8aR-1-substituted-6-oxodecahydroquinoline.

Wong and Foreman, Ser. No. 575,126 filed 1-30-84, now U.S. Pat. No. 4,528,290, have discovered that the other enantiomers; the tautomers Vb and Vd when R' is H and R is methyl, ethyl, n-propyl or allyl have D-1 dopamine agonist activity. These enantiomers are prepared from 4aR,8aR-1-substituted-6-oxodecahydroquinoline.

The sequence of reactions from Reaction Scheme I is repeated in Reaction Scheme II below using one isomer, 4aR,8aR-1-substituted-6-oxodecahydroquinoline, to prepare the desired 4aR,8aR-4,4a,5,6,7,8,8a,9-octahydro 1H(and 2H)pyrazolo[3,4-g]quinoline.

Reaction Scheme II

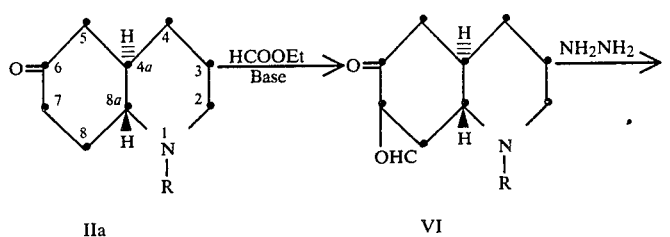

IIa          VI

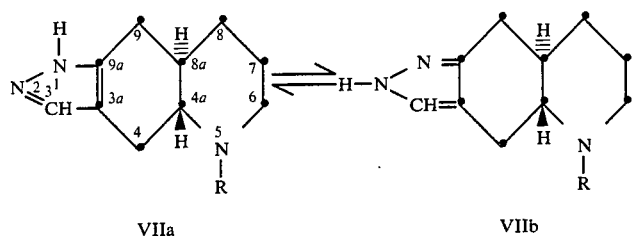

VIIa          VIIb where R has its previous meaning and VI represents four tautomeric forms-see IVa-d.

An additional advantage of the process set forth in Reaction Scheme II lies in the fact that the trans-dl-ketone (II) is resolved and the pure 4aR,8aR stereoisomer (IIa) is cyclized to yield an optically-active trans-4aR,8aR-octahydropyrazolo[3,4-g]quinoline, rather than cyclizing the trans-dl-racemate and resolving the trans-dl-pyrazoloquinoline. The same consideration applies to the preparation of the 4aS,8aS enantiomer, the D-1 agonist.

Other uses of the trans-dl racemate represented by II or of the individual enantiomers (where $R^1$ is H) represented by IIa and IIb, has been in the preparation of other active dopamine agonists. For example, the D-2 agonist trans-(+)-2-substituted-4-permissibly-substituted-6-lower alkyl or allyl-5,5a,6,7,8,9,9a,10-octahydropyrimido[4,5-g]quinoline and the 5aR,9aR enantiomer which are disclosed and claimed in Nichols et al Ser. No. 535,503 filed 9-26-83; now U.S. Pat. No. 4,501,890 are prepared from II or IIa. The D-1 dopamine agonistic 5aS,9aS enantiomer, claimed in Nichols et al, Ser. No. 606,091 filed 5-2-84 now abandoned, is prepared from IIb. The same intermediates can be used to prepare the trans-(±)-2-permissibly substituted-5-lower alkyl or allyl-permissibly substituted-5-lower alkyl or allyl-4,4a,5,6,7,8,8a,9-octahydrothiazolo[4,5-g]quinoline and the 4aR,8aR and 4aS,8aS enantiomers of Titus and Kornfeld, Ser. No. 604,687, filed 4-27-84, now U.S. Pat. No. 4,537,893 all dopamine agonists by reaction with an isothiourea, and the corresponding octahydro-oxazolo[4,5-g]quinoline of Schaus and Titus, Ser. No. 637,232, filed Aug. 2, 1984, now abandoned, continuation-in-part Ser. No. 743,198 filed June 10, 1985, where there is a 2-amino substituent, from the same intermediate and a permissibly substituted urea. This latter application of Schaus and Titus (loc. cit.) also provides a novel method of preparing certain of these octahydro-oxazolo[4,5]quinolines not preparable by any of the above procedures. According to this novel process, a 7-keto-1-lower alkyl or allyl decahydroquinoline is formylated via a Claissen reaction to yield a 6-formyl derivative (one of 4 tautomers). The formyl derivatives is then subjected to a Japp-Klingemann reaction with phenyldiazonium chloride to yield a 6-phenylhydrazone of the 6,7-dioxo-1-lower-alkyl or allyl decahydroquinoline. Hydrogenolysis of the phenylhydrazone gives a 6-amino-7-oxo derivative, acylation of which followed by cyclization with $POCl_3$, produces a 5-lower alkyl-4,4a,5,6,7,8,8a,9-octahydro-oxazolo[4,5-g]quinoline with H, lower alkyl etc at C-2. The 6-formylated derivatives of the 7-oxo-1-$C_{1-3}$ straight-chain alkyl or allyl decahydroquinoline can be represented by the following tautomeric forms Xa-d:

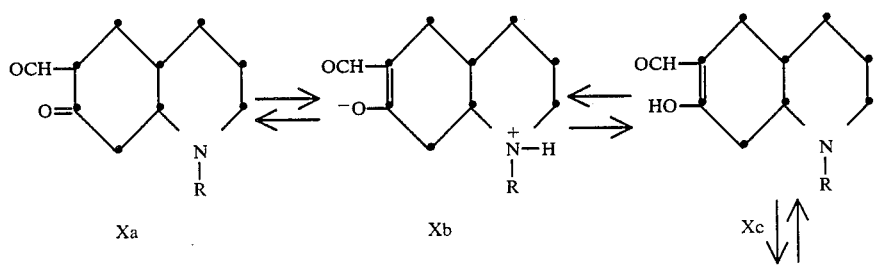

Xa          Xb          Xc

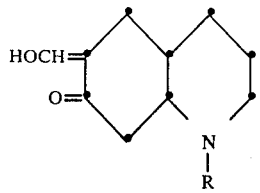

where R is $C_{1-3}$ straight chain alkyl, allyl or benzyl. All four tautomeric forms of the α-formylated 6 and 7-oxo derivates can be repr sented generically as follows:

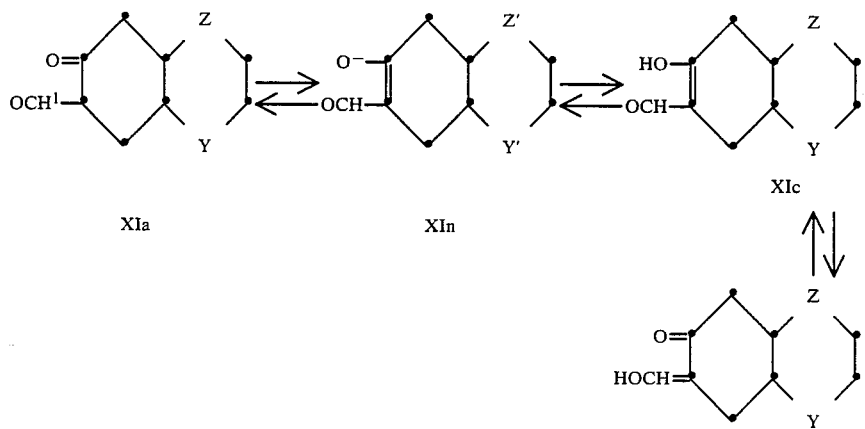

wherein one of Z and Y is —$CH_2$— and the other is —NR, wherein one of Z' and Y' is —$CH_2$— and the other is —$N^+HR$ and R has its previous meaning.

The processes of this invention are illustrated by the following specific examples.

EXAMPLE 1

One and one-half g. of potassium t-butoxide was weighed into a dry 250 ml. round-bottom flask. Twenty-five ml. of tetrahydrofuran (THF) were added to dissolve the potassium t-butoxide. Next, a solution containing 0.81 ml. of ethyl formate, 0.97 g. of trans-dl-1-n-propyl-6-oxodecahydroquinoline and 10 ml. of THF were added to the butoxide solution. The reaction mixture was maintained at ambient temperature for about 45 minutes. Two ml. of hydrazine were then added followed by sufficient 15% aqueous hydrochloric acid to lower the pH to about 9. The consequent reaction mixture was stirred for 30 minutes at ambient temperature at which time tlc indicated that no ketone starting material was present. The reaction mixture was then poured into dilute (10%) aqueous sodium hydroxide and the alkaline mixture extracted with methylene dichloride (equal volume). The extract was dried and the solvent removed by evaporation in vacuo to yield 1.31 g. of a yellow oil comprising crude trans-dl-5-n-propyl-4,4a,5,6,7,8,8a,9-octahydro-1H(and 2H)-pyrazolo[3,4-g]quinoline formed in the above reaction.

EXAMPLE 2

A sufficient amount of a 55% suspension of sodium hydride in mineral oil to yield 360 mg. (15 mmoles) of sodium hydride was placed in a 25 ml. round-bottom flask. The mineral oil was removed from the sodium hydride by thrice washing with hexane. The residual sodium hydride was then suspended in 6 ml. of THF.

Ethyl formate (740 mg.) plus one drop of anhydrous ethanol were next added followed by 975 mg. of trans-dl-1-n-propyl-6-oxodecahydroquinoline in 4 ml. of THF. The reaction mixture, which began to reflux almost immediately, was maintained at reflux temperature for about 45 minutes after which time tlc showed no remaining starting material. 50 ml. of water and 4 ml. of hydrazine were added and the pH adjusted with dilute aqueous hydrochloric acid to about pH=9. This reaction mixture was stirred at ambient temperature over night and was then poured into dilute aqueous sodium hydroxide. The precipitate consisting of 373 mg. of a white powder melting at 78°–84° C. was collected.

Analysis Calculated: C, 71.19; H, 9.65; N, 19.16; Found: C, 70.89; H, 9.15; N, 19.34.

Further material was obtained by adjusting the pH of the filtrate to about 13 with aqueous sodium hydroxide and extracting this alkaline solution with several portions of methylene dichloride. Concentration of the combined methylene dichloride extracts after drying yielded an additional 623 mg. of a white foam which was purified by chromatography over silica using THF containing a trace of aqueous ammonium hydroxide as the eluant. Early fractions shown to contain the desired pyrazolo[3,4-g]quinoline were combined to yield, after evaporation of the solvent, 437 mg. of a colorless oil.

This oil was converted to the dihydrochloride salt which melted at about 252°–263° C. after recrystallization from a methanol/acetone solvent mixture.

The above run was repeated except that 125 mg. of trans-(−)-(or 4aR,8aR)-n-propyl-6-oxodecahydroquinoline were used and the amounts of ethyl formate and base (sodium hydride in place of potassium t-butoxide) decreased proportionately. After the reaction was substantially complete, as shown by lack of starting material on tlc analysis, the reaction mixture was poured into dilute aqueous sodium hydroxide and the alkaline mixture extracted with methylene dichloride. Drying of the methylene dichloride extracted followed by removal of the solvent in vacuo yielded about 144 mg. of a colorless viscous oil which yielded only a single spot on tlc. The oil was dissolved in methanol and 0.20N aqueous hydrochloric acid added (3.2 ml.). Concentration of the resulting yellow solution yielded a yellow semi-solid material which was crystallized by dissolving in hot methanol and adding ether thereto to the point of incipient precipitation. 107 mg. of product thus obtained was dissolved in methanol. The methanol solution was decolorized with carbon and the carbon removed by filtration through celite. Evaporation of the solvent and recrystallization of the resulting residue from a methanol/ethyl acetate solvent mixture gave 80 mg. of a butter yellow powder—4aR,8aR-5-n-propyl-4,4a,5,6,7,8,8a,9-octahydro-1H(and 2H)-pyrazolo[3,4-g]quinoline; $[\alpha]_D^{25°} = -121.76°$. (MeOH, c=1)

EXAMPLE 3

A solution of 52 g. of optionally pure 4aR,8aR-1-n-propyl-6-oxodecahydroquinoline and 79 g. of ethyl formate in 250 ml. of THF was added to a solution of 59.8 g. of potassium t-butoxide in 600 ml. of THF previously cooled to about 0° C. Gas evolved during the addition. The reaction mixture was stirred at about 0° C. for one-half hour and at ambient temperature for an additional hour. Twenty-five and six tenths grams of hydrazine were added and the pH of the solution adjusted to pH~9 with 10% aqueous hydrochloric acid (about 500 ml.). This reaction mixture was stirred vigorously at ambient temperature for two hours, after which time it was poured into water. The aqueous mixture was made strongly basic (pH~13) with dilute aqueous sodium hydroxide. The alkaline mixture was extracted with methylene dichloride, and the methylene dichloride extract separated and dried. Evaporation of the solvent left a yellow foam as a residue which by tlc contained the desired pyrazoloquinoline plus a minor amount of a single impurity. The residue was dissolved in 1 l. of hot MeOH to which was added 250 ml. of 1N aqueous hydrochloric acid. Concentration of the solution yielded 65.4 g. of 4aR,8aR-5-n-propyl-4,4a,5,6,7,8-,8a,9-octahydro-1H(and 2H)-pyrazolo[3,4-g]quinoline hydrochloride as a light yellow solid. Recrystallization from methanol/ethyl acetate gave 51.7 g. (76% yield) of a slightly yellow granular solid; $[\alpha]_D^{25} = -121.0°$ (H$_2$O, c=1); $[\alpha]_{365}^{25} = -377.40$ (H$_2$O, c=1)

Analysis Calculated: C, 61.04; H, 8.67; N, 16.43; Cl, 13.86; Found: C, 61.32; H, 8.53; N, 16.22; Cl, 14.08.

The optically pure stereoisomeric starting material of Examples 2 and 3 was prepared by the procedure of Schaus and Booher, Ser. No. 439,107 filed 11-3-82, now U.S. Pat. No. 4,471,121.

EXAMPLE 4

Following the above procedure, 578 mg. of trans-(±)-1-n-propyl-7-oxodecahydroquinoline and 9.96 ml. of ethyl formate were dissolved in 10 ml. of THF, and the solution added to a solution of 866 mg. of potassium t-butoxide in 25 ml. of THF. The mixture thickened, and an additional 10 ml. of THF were added. The reaction mixture was then stirred for one hour.

The solution of trans-(±)-1-n-propyl-6-formyl-7-oxodecahydroquinoline thus prepared can be reacted directly with phenyldiazonium chloride by adjusting the pH of the solution to about 6 with 10% aqueous hydrochloric acid, adding a solution of aqueous sodium acetate followed by the addition of the phenyldiazonium chloride solution, as set forth in the application of Schaus and Titus, Ser. No. 637,232 filed this even date now abandoned, continuation-in-part application Ser. No. 743,198, filed 6-10-85.

The trans-(±)-1-n-propyl-7-oxodecahydroquinoline starting material of this example is conveniently prepared by the process of Schaus, Ser. No. 521,863 filed 8-10-83, by utilizing 7-hydroxyquinoline as a starting material rather than 6-hydroxyquinoline. An alternate preparation is found in the copending application of Huser, Schaus, Titus and Weigel, Ser. No. 637,181, filed this even date, now U.S. Pat. No. 4,600,777.

I claim:

1. A trans-dl tautomeric mixture represented by the formulas

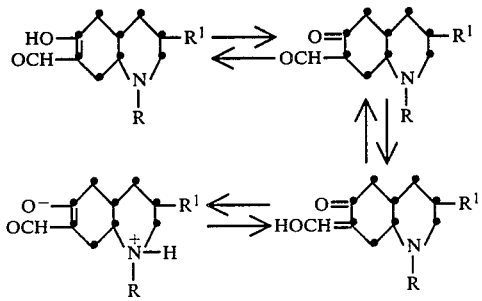

wherein R is C$_{1-3}$ alkyl, allyl or benzyl, and R$^1$ is H or COOQ wherein Q is H, C$_{1-2}$ alkyl or phenyl-substituted C$_{1-2}$ alkyl, or a salt thereof.

2. A tautomeric mixture according to claim 1 in which R is n-propyl and R$^1$ is H.

3. A tautomeric mixture according to claim 1 of 4aR,-8aR-1-n-propyl-6-oxo-7-formyldecahydroquinoline.

4. A tautomeric mixture according to claim 1 of 4aS,-8aS-1-n-propyl-6-oxo-7-formyldecahydroquinoline.

5. A tautomeric mixture according to claim 1 of trans-dl-1-n-propyl-6-oxo-7-formyldecahydroquinoline.

6. A trans-dl tautomeric mixture represented by the formulas

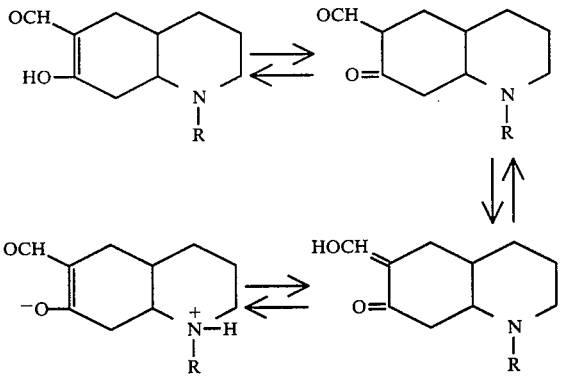

wherein R is C$_1$–C$_3$ alkyl, allyl, or benzyl, or a salt thereof.

7. A tautomeric mixture according to claim 6 in which R is n-propyl.

8. A tautomeric mixture according to claim 6 of 4aR,-8aR-1-n-propyl-6-formyl-7-oxodecahydroquinoline.

* * * * *